United States Patent
Moszner et al.

(10) Patent No.: US 9,833,389 B2
(45) Date of Patent: Dec. 5, 2017

(54) ADHESIVE DENTAL MATERIALS WITH STRONGLY ACIDIC ADHESIVE POLYMERS

(71) Applicant: Ivoclar Vivadent AG, Schaan (LI)

(72) Inventors: Norbert Moszner, Mauren (LI); Thorsten Bock, Feldkirch (AT); Yohann Catel, Buchs (CH); Doris Pospiech, Dresden (DE); Sandra Starke, Dresden (DE); Brigitte Voit, Dresden (DE)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/214,823

(22) Filed: Jul. 20, 2016

(65) Prior Publication Data

US 2017/0020791 A1    Jan. 26, 2017

(30) Foreign Application Priority Data

Jul. 22, 2015  (EP) .................................... 15177927

(51) Int. Cl.
| | |
|---|---|
| *C08F 2/46* | (2006.01) |
| *C08G 61/04* | (2006.01) |
| *A61K 6/083* | (2006.01) |
| *A61K 6/00* | (2006.01) |
| *C08F 220/40* | (2006.01) |

(52) U.S. Cl.
CPC .......... *A61K 6/0835* (2013.01); *A61K 6/0017* (2013.01); *A61K 6/0023* (2013.01); *A61K 6/0052* (2013.01); *A61K 6/0088* (2013.01); *A61K 6/083* (2013.01); *C08F 220/40* (2013.01)

(58) Field of Classification Search
CPC .. A61K 6/0835; A61K 6/0052; A61K 6/0023; A61K 6/0088; A61K 6/0017; A61K 6/083; C08F 220/40; C08L 33/02
USPC ........................................ 522/171, 1; 520/1
See application file for complete search history.

(56) References Cited

U.S. PATENT DOCUMENTS

| | | | |
|---|---|---|---|
| 3,872,047 A | 3/1975 | Jandourek | |
| 5,130,347 A | 7/1992 | Mitra | |
| 6,281,271 B1 * | 8/2001 | Rumphorst | A61K 6/005 522/71 |
| 6,902,608 B2 | 6/2005 | Erdmann et al. | |
| 7,683,103 B2 * | 3/2010 | Sawada | A61K 6/0017 433/217.1 |
| 8,129,444 B2 * | 3/2012 | Hecht | C09J 4/00 106/35 |
| 9,539,065 B2 * | 1/2017 | Cinader, Jr. | A61C 7/14 |
| 2001/0044513 A1 * | 11/2001 | Moszner | A61K 6/0023 526/278 |
| 2004/0254260 A1 * | 12/2004 | Mikulla | A61K 6/0835 523/116 |
| 2014/0296364 A1 * | 10/2014 | Moszner | A61K 6/0023 522/171 |
| 2015/0238390 A1 * | 8/2015 | Klee | A61K 6/0038 523/116 |

FOREIGN PATENT DOCUMENTS

| | | |
|---|---|---|
| CA | 2199567 C | 1/2003 |
| EP | 0323120 A2 | 7/1989 |
| EP | 2633847 A2 | 9/2013 |

OTHER PUBLICATIONS

Viohl, J., et al., "The chemistry of dental filling plastics," Carl Hanser Verlag, Munich Vienna, 1986, 8 pages.
Peutzfeldt, A., "Resin composites in dentistry: the monomer systems," European Journal of Oral Sciences, 105 (1997) 97-116.
Nicholson, John W., et al., "The Chemistry of Modern Dental Filling Materials," J. Chem Ed. vol. 76, No. 11, (Nov. 1999) 1497-1501.
Stansbury, J. W., "Curing Dental Resins and Composites by Photopolymerization," J. Esthet. Dent., vol. 12, No. 6, (2000), 300-308.
Moszner, N., et al., "New Polymer-Chemical Developments in Clinical Dental Polymer Materials: Enamel-Dentin Adhesives and Restorative Composites," J. Polym. Sci. Part A: Polym. Chem. 50 (2012) 4369-4402.
Moszner, N., et al., "Chemical aspects of self-etching enamel-dentin adhesives: A systematic review," Dent. Mat. (2005) 21, 895-910.

* cited by examiner

*Primary Examiner* — Jessica E Whiteley
(74) *Attorney, Agent, or Firm* — Ann M. Knab; Thad McMurray

(57) ABSTRACT

Radically polymerizable dental material which contains at least one radically polymerizable oligomer or polymer with strongly acidic groups, which has a number-average molecular weight of 1,000 to 200,000 g/mol.

19 Claims, No Drawings

ADHESIVE DENTAL MATERIALS WITH STRONGLY ACIDIC ADHESIVE POLYMERS

CROSS-REFERENCE TO RELATED APPLICATIONS

This application claims priority to European patent application No. 15177927.9 filed on Jul. 22, 2015, the disclosure of which is incorporated herein by reference in its entirety.

TECHNICAL FIELD

The present invention relates to dental materials which contain strongly acidic adhesive polymers and which are suitable in particular as dental adhesives, coating materials, filling composites and cements.

BACKGROUND OF THE INVENTION

Dental materials curable by radical polymerization usually contain a polymerizable organic matrix and one or more fillers. In most cases, a mixture of monomers, initiators, stabilizers, pigments and further additives is used as polymerizable organic matrix (J. Viohl, K. Dermann, D. Quast, S. Venz, Die Chemie zahnärztlicher Füllungskunststoffe [The chemistry of dental filling plastics], Carl Hanser Verlag, Munich-Vienna 1986, 21-27). Such materials can be cured by thermal, redox-initiated or light-induced radical polymerization. Acidic monomers are also being used increasingly for the preparation of dental materials. These give the materials self-etching properties and improve their adhesion to the natural tooth substance.

Mixtures of dimethacrylates are usually used as resins (cf. A. Peutzfeldt, Resin composites in dentistry: the monomer systems, Eur. J. Oral Sci. 105 (1997) 97-116; J. W. Nicolson, H. M. Anstice, The chemistry of modern dental filling materials, J. Chem. Ed. 76 (1999) 1497-1501; J. W. Stansburry, Curing dental resins and composites by photopolymerization, J. Esthet. Dent. 12 (2000) 300-308; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 50 (2012) 4369-4402).

In the case of adhesives, bisacrylamides are often used as cross-linker and acid group-containing methacrylates are mostly used as adhesive monomer (N. Moszner, U. Salz, J. Zimmermann, Chemical aspects of self-etching enamel-dentin adhesives: A systematic review, Dent. Mat. 21 (2005) 895-910). Examples of cross-linking dimethacrylates are 2,2-bis[4-(2-hydroxy-3-methacryloyloxypropyl)phenyl] propane (bis-GMA), 1,6-bis-[2-methacryloyloxyethoxycarbonylamino]-2,4,4-trimethylhexane (UDMA), decanediol-1,10-dimethacrylate, bismethacryloyloxy-methyltricyclo [5.2.1.]decane and triethylene glycol dimethacrylate (TEGDMA).

Acid monomers used commercially in dental materials are methacryloyloxydecyl dihydrogen phosphate (MDP), 2-methacryloyloxyethyl dihydrogen phosphate, 4-methacryloyloxyethyl trimellitic acid, 2-[4-dihydroxyphosphoryl)-2-oxabutyl]acrylic acid ethyl ester (EAEPA) and 2-acrylamido-2-methyl-1-propanesulphonic acid. It is known that acidic groups can etch and abrade the surface of the tooth structure, which leads to a mechanically improved substrate adhesion to the tooth structure. Moreover, acid groups can ionically bind the $Ca^{2+}$ cations of the dentin/enamel surface, which also leads to an improved adhesion to the tooth structure.

In addition to acidic monomers, organic polymers with acidic groups are also regularly used for the preparation of dental materials. They are primarily used for the preparation of glass ionomer cements. These are dental cements which cure by means of an ionic reaction between the acidic groups of the polymer and an ion-releasing filler component. EP 0 323 120 B1 discloses glass ionomer cements which contain polymers which have, on the one hand, ionic groups for the ionic curing reaction and, on the other hand, light-curable groups. The ionic groups are carboxyl groups.

EP 0 796 607 B1 discloses the preparation of functionalized weakly acidic polycarboxylic acids by ring-opening metathesis polymerization (ROMP) of a monomer mixture of methacrylic acid-(5-norbornene-2-endo/exo-methyl)ester and bicyclo[2,2,1]hept-5-ene-2,3-endo/exo-dicarboxylic acid bis(tetrahydropyran-2-yl)ester followed by splitting off of the tetrahydropyran protective groups. The polycarboxylic acids are characterized by a high adhesion to various substrates and are suitable in particular for the preparation of glass ionomer cements.

EP 0 951 896 B1 and corresponding U.S. Pat. No. 6,281,271, which is hereby incorporated by reference, disclose dental materials which contain acidic oligomers which, in addition to methacrylate groups, have carboxyl groups. The materials cure, on the one hand, by means of an acid-base reaction between acidic oligomer and ion-releasing filler and, on the other hand, by means of radical polymerization.

EP 2 633 847 A2 and corresponding US 20160143818, which is hereby incorporated by reference, disclose glass ionomer cements which contain a weakly acidic copolymer of acrylic acid and itaconic acid anhydride that also has carboxyl groups.

U.S. Pat. No. 3,872,047, which is hereby incorporated by reference, discloses dental primers which contain a solution of a polymer with polar and non-polar groups in alcohol. The polar groups are said to bind to metal-containing surfaces. The non-polar groups are radically polymerizable and can react with a dental restoration material that is applied to a layer of the primer.

SUMMARY OF THE INVENTION

The object of the invention is to provide dental materials which are characterized by a high and long-lasting adhesion to tooth structure, i.e. to tooth enamel and dentin. The dental materials are to have, moreover, a high storage stability which makes transport and storage of the dental materials possible without loss of activity.

DETAILED DESCRIPTION

The object is achieved according to the invention by dental materials which comprises at least one radically polymerizable oligomer or polymer with strongly acidic groups, preferably a radically polymerizable oligomer or polymer with phosphonic acid groups. The dental materials according to the invention can contain a mixture of different acidic radically polymerizable polymers.

By oligomers or polymers is meant compounds with a number-average molecular weight of preferably 1,000 to 200,000 g/mol, particularly preferably 10,000 to 100,000 g/mol. In the following, the compounds are uniformly called acidic polymers or polymers irrespective of the molecular weight.

According to the invention, by strongly acidic groups is meant, in particular, phosphonic acid groups. Other acidic groups are carboxylic acid groups, sulphonic acid groups, monohydrogen phosphate groups and dihydrogen phosphate groups. The acidic polymer can contain different types of acid groups. Acidic polymers which have exclusively phosphonic acid groups are preferred.

The strongly acidic groups can etch and thereby abrade the surface of the tooth structure, which leads to a mechanically improved adhesion to the tooth structure. Moreover, the acid groups can ionically bind $Ca^{2+}$ cations of the dentin/enamel surface, which also leads to an improvement in the adhesion. Within the framework of the present invention it was surprisingly found that polymers with strongly acidic groups lead to a significantly higher adhesion to the tooth structure than a corresponding amount of acidic monomers, i.e. in the case of a comparable concentration of acid groups a significantly better adhesion of the dental materials to the tooth structure is achieved.

The acidic polymers used according to the invention are radically polymerizable, i.e. they contain at least one radically polymerizable group. Preferred radically polymerizable groups are (meth)acryl, (meth)acrylamide, vinyl and allyl groups, particularly preferred are methacryl and allyl groups. The acidic polymer can contain different types of polymerizable groups. Acidic polymers with one type of polymerizable groups are preferred. The polymerizable groups of the acidic polymers cause the polymers to be covalently bonded into the polymer network during the radical polymerization.

The proportion of polymerizable groups in the polymer is preferably 60 mol.-% in relation to the strongly acidic groups, particularly preferably 5-30 mol.-% are polymerizable groups in relation to the acid groups present.

Acidic polymerizable polymers with phosphonic acid groups, which have number-average molecular weights between 10,000 and 100,000 g/mol and which have methacryl and/or allyl groups as polymerizable side groups, are particularly preferred.

The polymerizable acidic polymers can be prepared using known synthesis methods. Thus, homopolymers with defined molecular weights can be prepared with the methods of radical polymerization or controlled radical polymerization, starting from the corresponding acid monomers or esters thereof. The acid monomers or esters thereof can contain one or more acid groups or ester groups per monomer molecule. In addition to esters, other acid derivatives can also be used, i.e. derivatives from which the acid group can be released. In the case of monomers which do not contain any free acid groups but derivatives thereof, the acid groups are released at a point after the polymerization in a suitable reaction, for example by hydrolysis.

In the case of phosphonic acid groups, (meth)acrylates with dialkyl or disilyl phosphonate groups bound like esters are particularly suitable as monomeric acid derivatives. After the polymerization of these monomers, the phosphonic acid groups can be easily released therefrom, in the case of the disilyl phosphonate groups for example by simple reaction with water or methanol. Preferred polymerizable phosphonate derivatives are e.g. 3-(dimethoxyphosphoryl)propyl (meth)acrylate, 3-[di(trimethylsilyl)phosphoryl]propyl (meth)acrylate, 2-(di-methoxyphosphoryl)ethyl (meth)acrylate, 2-[di(trimethylsilyl)-phosphoryl]ethyl (meth)acrylate, 2-[4-(dimethoxyphosphoryl)-2-oxa-butyl]acrylic acid methyl ester and 2-[4-(dimethoxy-phosphoryl)-2-oxa-butyl] acrylic acid ethyl ester.

By using monomer mixtures which contain comonomers in addition to the acid group-containing monomers, statistical copolymers are easy to obtain. Preferred comonomers are methyl, ethyl, 2-hydroxyethyl, 2-hydroxypropyl, n-butyl, benzyl, tetrahydrofurfuryl and isobornyl (meth)acrylate as well as 2-acetoacetoxyethyl methacrylate.

By incorporating comonomers into the polymer chain it is possible to influence the polymer properties in a targeted manner, e.g. the wetting behaviour or the solubility. For example, the incorporation of comonomers with polar groups such as 2-hydroxyethyl methacrylate improves the solubility in water or alcohols, while the incorporation of comonomers with non-polar groups such as n-butyl methacrylate, benzyl methacrylate or tetrahydrofurfuryl methacrylate improves the solubility in acetone or ethyl acetate.

Acid group-containing sequential or block copolymers can also be obtained using the methods of controlled radical polymerization or by sequential anionic polymerization of corresponding acid monomer derivatives and subsequent release of the acid groups.

The insertion of polymerizable groups preferably takes place by reaction of the acid group-containing polymers obtained with suitably functionalized polymerizable monomers, for example with 2-hydroxyethyl (meth)acrylate, allyl alcohol, N-(methyl)-N-(2-hydroxyethyl)acrylamide, N-(5-hydroxypentyl)methacrylamide or glycidyl methacrylate.

A specific example is the radical homopolymerization of 2-[4-(dihydroxyphosphoryl)-2-oxa-butyl]-acrylic acid ethyl ester with azobisisobutyronitrile (AIBN) as initiator and the subsequent polymer-analogous reaction with glycidyl methacrylate (GMA) in a one-pot reaction:

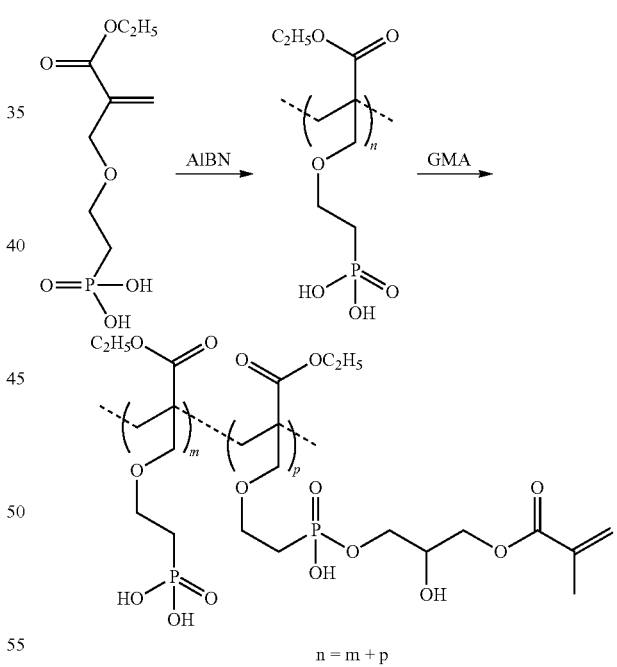

$n = m + p$

By a polymer-analogous reaction is meant a reaction in which a polymer as substrate is reacted while preserving the degree of polymerization, i.e. without changing the number of monomer building blocks, for example by reacting functional groups of the polymer to form other groups without otherwise changing the polymer structure (no degradation and no cross-linking).

The proportion of acid groups which is reacted here is preferably chosen such that the proportion of polymerizable groups in the polymer is up to 60 mol.-% in relation to the phosphonic acid groups, particularly preferably 5-30 mol.-% are polymerizable groups in relation to the phosphonic acid groups present.

Alternatively, the polymerizable groups can also be inserted by polymer-analogous reaction of the comonomer component. For the insertion of polymerizable groups by means of polymer-analogous reaction, OH group-containing monomers such as 2-hydroxyethyl (meth)acrylate, hydroxypropyl (meth)acrylate or allyl alcohol are particularly suitable, wherein the OH groups of the formed polymers can be reacted polymer-analogously with 2-isocyanatoethyl methacrylate.

A specific example of this is the radical copolymerization of 2-[4-(dimethoxyphosphoryl)-2-oxa-butyl]-acrylic acid ethyl ester and 2-hydroxyethyl methacrylate (HEMA) with AIBN as initiator, subsequent polymer-analogous reaction (or partial reaction) of the OH groups with 2-isocyanatoethyl methacrylate (IEMA), splitting off of the ester groups by reaction with trimethylsilyl bromide (TMSBr) and then with methanol:

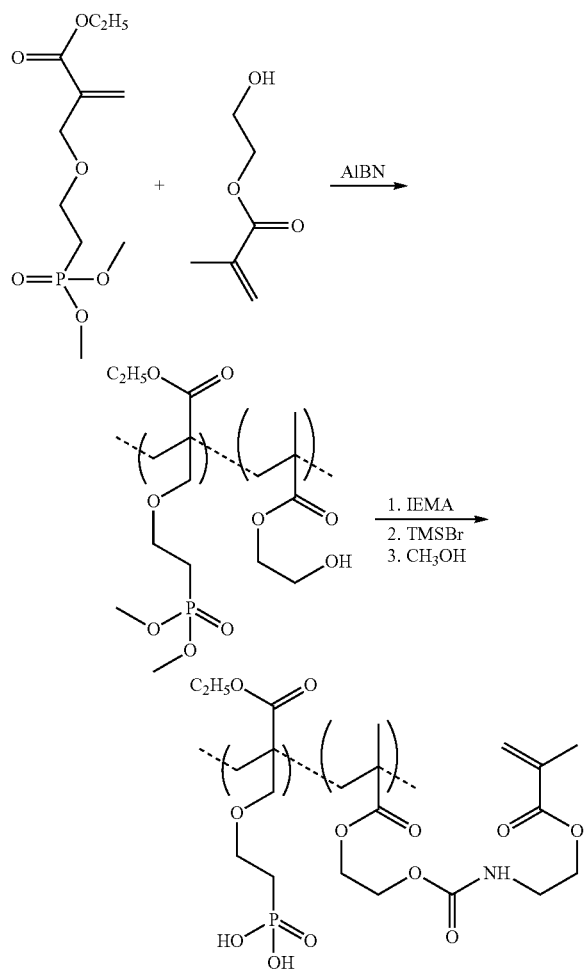

Alternatively, the polymers according to the invention can also be prepared such that first an isocyanate group-containing monomer such as 2-isocyanatoethyl methacrylate is radically homopolymerized. The homopolymer is then reacted polymer-analogously with a hydroxyl group-containing methacrylate such as e.g. HEMA, and a hydroxyl group-containing phosphonic acid dimethyl ester such as 2-hydroxyethylphosphonic acid dimethyl ester, preferably with a mixture of 2-hydroxyethyl methacrylate (HEMA) and 2-hydroxyethylphosphonic acid dimethyl ester. In the third step, the phosphonic acid groups are then released, e.g. by reaction of the phosphonate groups with TMSBr and then with methanol.

The acidic polymers used according to the invention are preferably poly(meth)acrylates, particularly preferably poly (meth)acrylates which can be obtained by means of radical polymerization of the above-named acidic monomers and optionally comonomers and optionally subsequent polymer-analogous reactions. The poly(meth)acrylates have acidic and radically polymerizable side groups.

The acidic polymers are characterized in that, on the one hand, they contain a sufficient number of free acid groups per polymer molecule to ensure the desired substrate adhesion to the tooth structure and, on the other hand, a sufficient number of polymerizable groups is present in order that the acidic polymers can be covalently bonded into the polymer network of the dental materials during curing.

The acidic polymers according to the invention are very soluble in alcohols, such as e.g. ethanol and acetone, or in aqueous mixtures of alcohols or of acetone. In addition, they can be mixed well with radically polymerizable monomers and exhibit a good radical copolymerizability. They give dental materials a good adhesion to the tooth structure, i.e. to enamel and dentin, and thus represent an important adhesive component.

Moreover, the polymers according to the invention are characterized by good film-forming properties. This is advantageous in particular in the case of use in dental adhesives. Film formation ensures a uniform layer formation of the adhesive when applied and improves the technical tolerance. For example, a good film formation reduces the risk of the liquid adhesive layer being damaged or even completely removed when the solvent is blown with compressed air.

The acidic polymers according to the invention are particularly suitable for the preparation of adhesive dental materials such as adhesives, cements or coating materials.

According to the invention, those dental materials are preferred which additionally comprise at least one further radically polymerizable monomer. It was shown that the strongly acidic adhesive polymers according to the invention have good compatibility with conventional dental monomers and produce stable mixtures which produce materials with very good adhesive and mechanical properties in the case of polymerization. The dental materials according to the invention have a stability which makes safe transport and safe storage possible.

As additional radically polymerizable monomers or mixtures of radically polymerizable monomers, (meth)acrylates are preferred, mixtures of mono- and polyfunctional (meth) acrylates are particularly preferred, and mixtures of mono- and difunctional (meth)acrylates are quite particularly preferred. By mono(meth)acrylates is meant compounds with one radically polymerizable group, by di- and polyfunctional (meth)acrylates is meant compounds with two or more, preferably 2 to 4, radically polymerizable groups. In all cases, methacrylates are preferred to acrylates.

Preferred mono- or polyfunctional (meth)acrylates are methyl, ethyl, 2-hydroxyethyl, 2-hydroxypropyl, n-butyl, benzyl, tetrahydrofurfuryl or isobornyl (meth)acrylate, 2-acetoacetoxyethyl methacrylate, p-cumylphenoxyethylene glycol methacrylate (CMP-1E), bisphenol A di(meth)acrylate, bis-GMA (an addition product of methacrylic acid and bisphenol A diglycidyl ether), UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), bis(methacryloyloxymethyl)tricyclo[5.2.1.]decane (TCDMA), ethoxylated or propoxylated bisphenol A di(meth)acrylate, such as e.g. the bisphenol A dimethacrylate 2-[4-(3-methacryloyloxyethoxy-ethyl)phenyl]-2-[4-(3-methacryloyloxyethyl)phenyl]-propane) (SR-348C) with 3 ethoxy groups or 2,2-bis[4-(2-(meth)acryloxypropoxy)phenyl]propane, di-, tri- or tetraethylene glycol di(meth)acrylate, trimethylolpropane tri(meth)acrylate, penta-erythritol tetra(meth)acrylate, as well as glycerol di(meth)-acrylate acetate, glycerol di(meth)acrylate, 1,4-butanediol di(meth)acrylate, 1,10-decanediol di(meth)acrylate or 1,12-dodecanediol di(meth)acrylate or glycerol trimethacrylate (GTMA).

N-mono- or -disubstituted acrylamides, such as e.g. N-ethyl acrylamide, N,N-dimethyl acrylamide, N-(2-hydroxyethyl)acrylamide or N-methyl-N-(2-hydroxyethyl)acrylamide, or N-monosubstituted methacrylamides, such as e.g. N-ethylmethacrylamide or N-(2-hydroxyethyl)methacrylamide as well as N-vinylpyrrolidone or allyl ether are further preferred. These monomers are characterized by a low viscosity and a high hydrolytic stability and are particularly suitable as diluting monomers.

Cross-linking pyrrolidones, such as e.g. 1,6-bis(3-vinyl-2-pyrrolidonyl)-hexane or commercially available bisacrylamides, such as methylene- or ethylenebisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)piperazine, which can be synthesized by reaction from the corresponding diamines with (meth)acrylic acid chloride, are also preferred. These monomers are characterized by a high hydrolytic stability and are particularly suitable as cross-linking monomers.

Particularly preferred monomers are: CMP-1E, bis-GMA, UDMA, TMX-UDMA, TCDMA, ethoxylated or propoxylated bisphenol A dimethacrylate, SR-348c, triethylene glycol dimethacrylate, glycerol dimethacrylate, 1,10-decanediol dimethacrylate or glycerol trimethacrylate (GTMA) as well as N,N'-diethyl-1,3-bis(acrylamido)-propane. A further preferred monomer is maleic acid anhydride.

According to the invention it was surprisingly found that optimum adhesion to tooth enamel and dentin can be achieved by combining the acidic polymers with acidic monomers. The dental materials according to the invention therefore preferably also contain one or more acid group-containing radically polymerizable monomers (adhesive monomers; acidic monomers). Radically polymerizable oligomers or polymers which have carboxylic acid groups, sulphonic acid groups, monohydrogen phosphate groups or dihydrogen phosphate groups are also very suitable in combination with acidic monomers. Acidic polymers with phosphonic acid groups are, however, also quite particularly preferred here. Materials are particularly advantageous which, in addition to at least one acidic polymer and at least one acidic monomer, additionally contain at least one non-acidic monomer.

Preferred acid group-containing monomers are polymerizable carboxylic acids, phosphonic acids, phosphoric acid esters and sulphonic acids.

Preferred carboxylic acids are maleic acid, acrylic acid, methacrylic acid, 2-(hydroxymethyl)acrylic acid, 4-(meth)acryl-oyloxyethyltrimellitic acid, 10-methacryloyloxydecylmalonic acid, N-(2-hydroxy-3-methacryloyloxypropyl)-N-phenylglycine and 4-vinylbenzoic acid.

Preferred phosphonic acid monomers are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methylpentylphosphonic acid, 2-[4-(dihydroxyphosphoryl)-2-oxa-butyl]-acrylic acid or 2-[4-(dihydroxyphosphoryl)-2-oxa-butyl]-acrylic acid ethyl and -2,4,6-trimethyl phenyl ester.

Preferred acidic polymerizable phosphoric acid esters are 2-methacryloyloxypropyl mono- or dihydrogen phosphate, 2-methacryloyloxyethyl mono- or dihydrogen phosphate, 2-methacryloyloxy-ethylphenyl hydrogen phosphate, dipentaerythritol pentamethacryloyloxyphosphate, 10-methacryloyloxydecyl dihydrogen phosphate, phosphoric acid mono-(1-acryloyl-piperidin-4-yl) ester, 6-(methacrylamido)hexyl dihydrogen phosphate and 1,3-bis-(N-acryloyl-N-propyl-amino)-propan-2-yl dihydrogen phosphate.

Preferred polymerizable sulphonic acids are vinylsulphonic acid, 4-vinylphenylsulphonic acid or 3-(methacrylamido)propylsulphonic acid.

Particularly preferred acid monomers are 4-(meth)acryloyloxy-ethyltrimellitic acid anhydride, 10-methacryloyloxydecylmalonic acid, 2-methacryloyloxyethylphosphonic acid, 2-methacrylamidoethylphosphonic acid, 2-[4-(dihydroxyphosphoryl)-2-oxa-butyl]acrylic acid, 2-[4-(dihydroxyphosphoryl)-2-oxa-butyl]-acrylic acid ethyl or -2,4,6-trimethyl phenyl ester, 2-methacryloyloxypropyl mono- or dihydrogen phosphate, 2-methacryloyloxyethyl mono- or dihydrogen phosphate, 2-methacryloyloxy-ethylphenyl hydrogen phosphate, 10-methacryloyloxydecyl dihydrogen phosphate, 6-(methacrylamido)hexyl dihydrogen phosphate and 1,3-bis-(N-acryloyl-N-propyl-amino)-propan-2-yl dihydrogen phosphate.

The dental materials according to the invention preferably also comprise an initiator for the radical polymerization, particularly preferably a photoinitiator.

Benzophenone, benzoin and derivatives thereof or α-diketones or derivatives thereof, such as 9,10-phenanthrenequinone, 1-phenyl-propane-1,2-dione, diacetyl or 4,4'-dichlorobenzil are preferred for the initiation of the radical photopolymerization. Camphorquinone and 2,2-dimethoxy-2-phenyl-acetophenone are particularly preferably used and α-diketones in combination with amines as reducing agent, such as e.g. 4-(dimethylamino)benzoic acid ethyl ester, N,N-dimethylaminoethyl methacrylate, N,N-dimethyl-sym.-xylidine or triethanolamine are particularly preferably used. Norrish type I photoinitiators, above all acyl- or bisacylphosphine oxides, monoacyltrialkyl or diacyldialkyl germanium compounds, such as e.g. benzoyltrimethylgermanium, dibenzoyldiethylgermanium or bis(4-methoxybenzoyl)diethylgermanium are also particularly suitable. Advantageously, mixtures of the different photoinitiators can also be used, such as e.g. dibenzoyldiethylgermanium in combination Thermal initiators, such as azo compounds, e.g. azobisisobutyronitrile, or peroxides, e.g. dibenzoyl peroxide and benzopinacol and 2,2'-dialkylbenzopinacols, are preferred as initiators for hot curing.

Preferably, redox-initiator combinations, such as e.g. combinations of benzoyl peroxide with N,N-dimethyl-sym.-xylidine or N,N-dimethyl-p-toluidine, are used as initiators for a polymerization carried out at room temperature. In addition, redox systems consisting of peroxides or hydroperoxides and reducing agents such as e.g. ascorbic acid, barbiturates, thioureas or sulphinic acids are also particularly suitable.

Photopolymerizable dental materials are preferably present in the form of a single mixture which contains all the constituents of the dental material. They contain exclusively a photoinitiator as initiator and can be cured by irradiation with light.

In addition to the photoinitiator, dual-curing dental materials additionally contain a peroxide, preferably hydroperoxide, as oxidizing agent. Dual-curing materials are preferably present in the form of two separate mixtures, as otherwise a premature curing would take place, wherein the first mixture preferably contains the (hydro)peroxide and the second mixture preferably contains the thiourea derivative. The thiourea derivative serves as reducing agent (accelerator). The mixtures are correspondingly also called catalyst paste and accelerator paste. A mixture can, in this connection, also consist of only a single component or a single constituent. The curing of the dual-curing materials can be activated by mixing the catalyst and accelerator pastes. The composition is adjusted such that it still remains processable for a few minutes after the pastes are mixed (so-called processing time), but cures rapidly after the processing. The processing and curing times can be adjusted primarily through the type and concentration e.g. of (hydro)peroxide, thiourea derivative and optionally by the addition of further components such as transition metal redox catalyst and inhibitor.

As a rule, a polymerization activated by redox-initiator systems proceeds more slowly than a photopolymerization. Correspondingly, excesses can be removed easily in the case of dual-curing materials, the radiation-activated photopolymerization is initiated after excesses have been removed.

Furthermore, the dental materials according to the invention preferably also comprise at least one organic or particularly preferably inorganic particulate filler or mixtures thereof. The filler is preferably added to improve the mechanical properties and to adapt the viscosity. Amorphous spherical materials based on oxides are preferred as fillers, such as $SiO_2$, $ZrO_2$ and $TiO_2$ or mixed oxides of $SiO_2$, $ZrO_2$, ZnO and/or $TiO_2$, nanoparticulate or microfine fillers such as pyrogenic silica or precipitated silica (weight-average particle size of 10-1,000 nm) as well as mini fillers, such as quartz, glass ceramic or X-ray opaque glass powders of e.g. barium or strontium aluminium silicate glasses (weight-average particle size of 0.01-10 μm, particularly preferably 0.01-1 μm, quite particularly preferably 0.2-1 μm). Further preferred fillers are X-ray opaque fillers, such as ytterbium trifluoride or nanoparticulate tantalum(V) oxide or barium sulphate or mixed oxides of $SiO_2$ with ytterbium(III) oxide or tantalum(V) oxide (weight-average particle size of 10-1,000 nm). The dental materials according to the invention preferably do not contain any ion-releasing fillers, in particular any $Ca^{2+}$- or $Al^{3+}$-releasing glasses.

To improve the bond between the filler particles and the cross-linked polymerization matrix, $SiO_2$-based fillers can be surface-modified with methacrylate-functionalized silanes, such as e.g. 3-methacryloyoxypropyltrimethoxysilane. For the surface-modification of non-silicate fillers, e.g. of $ZrO_2$ or $TiO_2$, functionalized acidic phosphates, such as e.g. 10-methacryloyloxy dihydrogen phosphate, can also be used.

Depending on the desired intended use, the dental materials according to the invention can preferably also contain solvent, in particular water, ethanol or a mixture thereof.

Optionally, the compositions used according to the invention can also contain further additives, above all stabilizers, such as e.g. polymerization stabilizers, flavourings, dyes, microbiocidal active ingredients, fluoride ion-releasing additives, optical brighteners, fluorescent agents, plasticizers and/or UV absorbers.

According to the invention, those dental materials which have the following composition are particularly preferred:
a) 0.1 to 30 wt.-%, preferably 1 to 30 wt.-% and particularly preferably 2 to 20 wt.-% of at least one acidic polymer,
b) 0.01 to 10 wt.-%, preferably 0.1 to 3.0 wt.-% and particularly preferably 0.5 to 3.0 wt.-% initiator(s),
c) 1 to 40 wt.-%, preferably 2 to 30 wt.-% and particularly preferably 5 to 20 wt.-% acidic radically polymerizable monomer(s),
d) 1 to 80 wt.-%, preferably 1 to 60 wt.-% and particularly preferably 5 to 50 wt.-% other radically polymerizable monomer(s), and
e) 0 to 70 wt.-%, preferably, depending on the use, 0 to 20 wt.-% (adhesive) or 10 to 70 wt.-% (adhesive cement), particularly preferably, depending on the use, 1 to 15 wt.-% (adhesive) or 15 to 60 wt.-% (adhesive cement) filler(s).

Dental materials for use as adhesives or adhesive coating materials preferably also contain in addition:
f) 0 to 70 wt.-%, preferably 0 to 60 wt.-% and particularly preferably 0 to 50 wt.-% solvent, preferably water.

Dental materials for use as adhesives or adhesive coating materials preferably have the following composition:
a) 0.1 to 30 wt.-%, preferably 1 to 30 wt.-% and particularly preferably 2 to 20 wt.-% of at least one acidic polymer,
b) 0.01 to 10 wt.-%, preferably 0.1 to 3.0 wt.-% and particularly preferably 0.5 to 3.0 wt.-% initiator(s),
c) 1 to 30 wt.-%, preferably 2 to 30 wt.-% and particularly preferably 5 to 20 wt.-% acidic radically polymerizable monomer(s),
d) 1 to 80 wt.-%, preferably 1 to 60 wt.-% and particularly preferably 5 to 50 wt.-% other radically polymerizable monomer(s),
e) 0 to 20 wt.-% filler(s), and
f) 0 to 70 wt.-%, preferably 5 to 60 wt.-% and particularly preferably 10 to 50 wt.-% solvent, preferably water.

Dental materials for use as adhesive composite cements or filling composites preferably have the following composition:
a) 0.1 to 30 wt.-%, preferably 0.5 to 20 wt.-% and particularly preferably 1 to 10 wt.-% of at least one acidic polymer,
b) 0.01 to 10 wt.-%, preferably 0.1 to 3.0 wt.-% and particularly preferably 0.5 to 3.0 wt.-% initiator(s),
c) 1 to 30 wt.-%, preferably 2 to 20 wt.-% and particularly preferably 2 to 15 wt.-% acidic radically polymerizable monomer(s),
d) 1 to 60 wt.-%, preferably 0 to 50 wt.-% and particularly preferably 5 to 40 wt.-% other radically polymerizable monomer(s), and
e) 10 to 70 wt.-%, preferably 20 to 70 wt.-% and particularly preferably 40 to 70 wt.-% filler(s).

Unless otherwise indicated, all quantities relate to the total mass of the materials. The individual quantity ranges can be chosen separately.

Those dental materials which consist of the named substances are particularly preferred. Furthermore, those materials are preferred in which the individual substances are in each case selected from the above-named preferred and particularly preferred substances.

The dental materials according to the invention are particularly suitable as adhesives and adhesive coating materials, filling composites and cements.

The dental materials are suitable primarily for intraoral application by the dentist to restore damaged teeth, i.e. for therapeutic use, e.g. as adhesives or adhesive cements, filling composites, coating and veneering materials (clinical materials).

However, they can also be used extraorally, for example in the preparation or repair of dental restorations, such as inlays, onlays, crowns and bridges (technical materials).

The invention is explained in more detail below by means of embodiment examples.
m

EMBODIMENT EXAMPLES

Example 1

Synthesis of Strongly Acidic Adhesive Polymers With Polymerizable Groups a) Radical Copolymerization of 2-[4-(dimethoxy-phosphoryl)-2-oxa-butyl]-acrylic acid ethyl ester (DMPAME) and 2-hydroxyethyl methacrylate (HEMA)

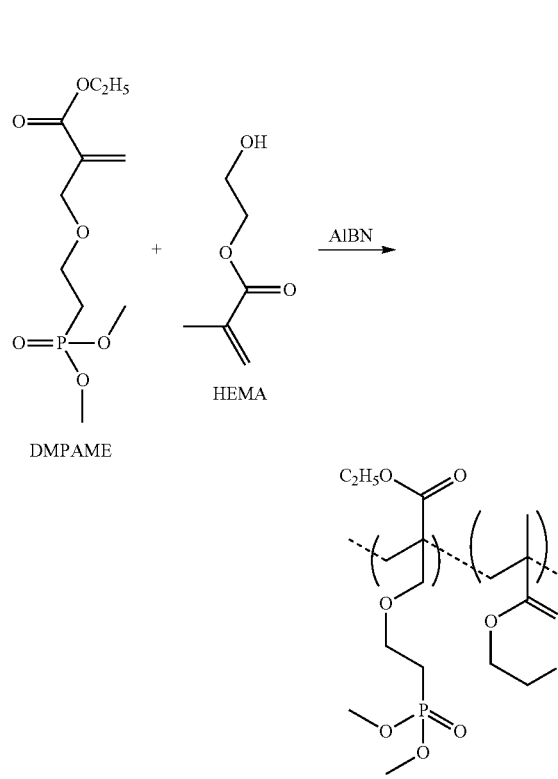

2.463 g of the initiator 2,2'-azobis(2-methylpropionitrile) (AIBN) were placed in a heated 500-ml Schlenk flask with a magnetic stirrer provided with a septum. After making inert three times (evacuating and flushing with nitrogen), 300 g of the solvent mixture ethanol/water (1/1 vol./vol.) as well as 35.137 g HEMA and 7.986 g of the phosphonic acid ester DMPAME were injected via the septum. The educt concentration in solution was thus 15 mass-%.

The reaction mixture was then completely degassed, the Schlenk flask was flushed with a nitrogen gas stream and the polymerization was started by immersion in a pre-tempered water bath. The solution was stirred for 5 h at 65° C. and the transparent, moderately viscous mixture obtained after the reaction had ended was dialyzed for 48 h in water and for a further 12 h in pure ethanol at room temperature. For this, a dialysis membrane consisting of regenerated cellulose, MW 1000 Da, was used. The product solution purified in this way was then concentrated to dryness and dried in a vacuum drying oven at room temperature under vacuum for one week. A yield of 39.541 g (87.2%) was able to be achieved. The determination of molecular weight by means of GPC gave: $M_n$: 56,000 g/mol, $M_w$: 248,000 g/mol. The composition was calculated from the $^1$H-NMR spectrum of the product. The determined composition was: 91/9 mol.-%/ mol.-% (HEMA/DMPAME).

b) Partial Polymer-Analogous Reaction of the OH Groups with 2-isocyanatoethyl methacrylate (IEMA)

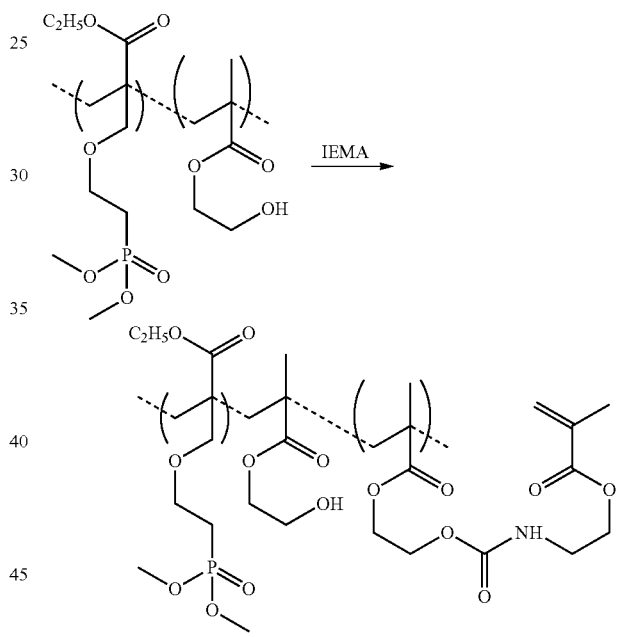

5.0316 g of the polymer obtained in stage a) as well as 0.1 g hydroquinone were weighed into a heated 250-ml Schlenk flask with a magnetic stirrer provided with a septum. After making the solid mixture inert, 70 g dimethyl sulphoxide as solvent was added via the septum under a nitrogen atmosphere. To improve the solubility of the mixture, the oil bath had already been tempered to 50° C. at this point. When all constituents were dissolved, 0.221 g dibutyltin dilaurate and 1.629 g IEMA were also carefully added dropwise via the septum. The educt concentration in solution was thus 10 mass-%. The pale yellow, transparent reaction mixture was stirred for 48 h at 50° C. under a continuous nitrogen gas stream and, after the end of the synthesis, dialyzed in ethanol for 120 h at room temperature. The concentrated product solution was dried for one week under vacuum at room temperature. A yield of 5.645 g (84.7%) was able to be achieved. The determination of molecular weight by means of GPC gave: $M_n$: 65,000 g/mol, $M_w$: 253,000 g/mol. The composition determined by means of $^1$H NMR spectroscopy was: 61/9/30 mol.-%/mol.-%/mol.-% (HEMA/DMPAME/IEMA reaction product).

c) Deprotection of the Phosphonic Acid Groups by Sequential Reaction with Trimethylsilyl Bromide (TMSBr) and Methanol

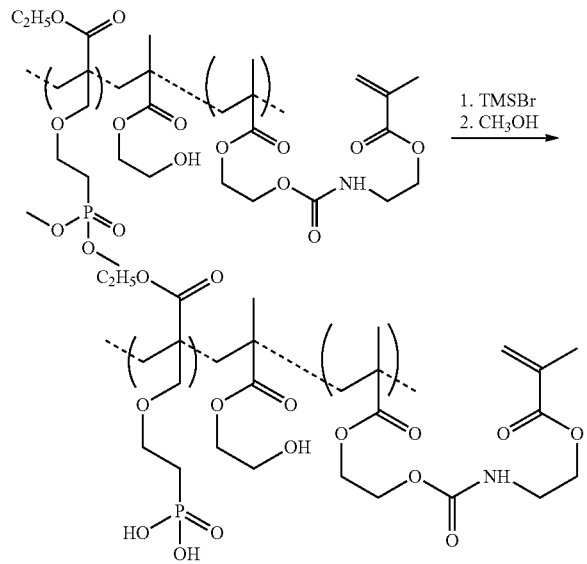

4.350 g of the dried terpolymer from pre-stage b) was placed in a 100-ml Schlenk flask equipped with a magnetic stirrer and septum and made inert three times. 53 g DMF was then added under a nitrogen atmosphere (starting concentration of the solution max. 30 mass-%). The TMSBr (1.194 g) was added after the polymer had dissolved completely and the pale yellow, transparent mixture was stirred at 30° C. for 5 h under inert gas. After the end of the reaction, 55 ml methanol was added and likewise stirred for 30 minutes. The volatile methanol and TMSBr were drawn off under vacuum accompanied by the addition of 0.02 g BHT and the remaining product solution was dialyzed in ethanol for 120 h. The product solution purified of DMF in this way was concentrated to dryness and dried in a vacuum drying oven at room temperature under vacuum for one week. A yield of 4.423 g (85.4%) of the phosphonic acid and methacrylate group-containing terpolymer was able to be achieved. The terpolymer obtained has a very good solubility in aqueous alcohol. The determination of molecular weight by means of GPC gave: $M_n$: 44,500 g/mol., $M_w$: 143,000 g/mol. The acquisition of a $^{31}$P spectrum of the product showed a shift of the phosphorus signal from 31.52 ppm (phosphonic ester) to 23.64 ppm (phosphonic acid). The calculation of the composition from the $^1$H-NMR spectrum gave: 61/9/30 mol.-%/mol.-%/mol.-% (HEMA/phosphonic acid/IEMA reaction product).

Example 2

Adhesive Based on the Strongly Acidic Adhesive Polymers From Example 1 and Adhesion Investigations For adhesion investigations, the following adhesives were prepared (Table 1):

TABLE 1

| Composition of the adhesives (values in wt.-%) | | |
|---|---|---|
| Component | Adhesive A | Adhesive B (comparison) |
| Terpolymer[1] | 4.50 | — |
| HEMA | 24.50 | 25.65 |
| Bis-GMA[2] | 23.50 | 24.61 |
| D$_3$MA[3] | 9.00 | 9.42 |
| MDPA[4] | 5.59 | 5.85 |
| Ethanol | 13.00 | 13.61 |
| Deionized water | 12.00 | 12.57 |
| Pyrogenic silicic acid[5] | 4.00 | 4.19 |
| Photoinitiator[6] | 3.80 | 3.98 |
| BHT | 0.11 | 0.11 |

[1]Terpolymer from Example 1,
[2]Bis-GMA (addition product of methacrylic acid and bisphenol A diglycidyl ether),
[3]Decane-1,10-diol dimethacrylate (D$_3$MA),
[4]10-Methacryloyloxydecyl dihydrogen phosphate (MDAP),
[5]Aerosil ® 200 (Evonik), spec. surface area 200 m$^2$/g,
[6]Mixture of camphorquinone (A: 1.80 wt.-% and B: 1.88 wt.-%), 4-dimethyl-benzoic acid ethyl ester (A: 1.0 wt.-% and B: 1.05 wt.-%) and 2-(dimethylamino)ethyl methacrylate (A: 1.0 wt.-% and B: 1.05 wt.-%).

To investigate dentin adhesion, bovine teeth were embedded in plastic cylinders such that the dentin and the plastic were in one plane. A layer of adhesive of the above composition was brushed on with a small brush (microbrush), the adhesive was moved on the tooth structure for approx. 20 s, briefly blown with an air blower to remove the solvent and exposed to light for 10 s with an LED lamp (Bluephase, Ivoclar Vivadent). A cylinder of a radically curing dental composite material (Tetric® EvoCeram; Ivoclar Vivadent AG) was polymerized onto the adhesive layer. The test pieces were then stored in water for 24 h at 37° C. and the adhesive shear strength was determined according to the ISO guideline "ISO 2003-ISO TR 11405: Dental Materials Guidance on Testing of Adhesion to Tooth Structure" (Table 2). The results for Adhesive A with the terpolymer from Example 1 show a significant improvement in adhesive strength on dentin in comparison with the polymer-free Adhesive B.

TABLE 2

| Dentin adhesion values | | |
|---|---|---|
| Adhesive | Dentin SBS (MPa) | Number of acid groups[1] |
| A | 33.4 ± 3.3 | 0.196 mmol/g |
| B (comparison) | 18.9 ± 0.9 | 0.182 mmol/g |

[1]Concentration of acid groups in Adhesives A and B, for Adhesive A based on the acid groups of the terpolymer and MDPA and for Adhesive B based on the acid groups of MDPA.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:
1. Radically polymerizable dental material which comprises
at least one radically polymerizable oligomer or polymer with strongly acidic phosphonic acid groups, which has a number-average molecular weight of 1,000 to 200,000 g/mol and which is prepared by
radical polymerization of at least one polymerizable phosphonate derivative which is selected from 3-(dimethoxy-phosphoryl)propyl (meth)acrylate, 3-[di(trim- ethylsilyl)-phosphoryl]propyl (meth) acrylate, 2-(dimethoxy-phosphoryl)ethyl (meth)acrylate, 2-[di(trimethylsilyl)-phosphoryl]ethyl (meth)acrylate, 2-[4-(dimethoxyphosphoryl)-2-oxa-butyl]acrylic acid methyl ester and 2-[4-(dimethoxyphosphoryl)-2-oxa-butyl]acrylic acid ethyl ester, followed by releasing the phosphonic acid groups by reaction with water or methanol, or by radical polymerization of a monomer mixture comprising at least one of said polymerizable phosphonate derivatives and at least one comonomer which is selected from methyl, ethyl, 2-hydroxyethyl, 2-hydroxypropyl, n-butyl, benzyl, tetrahydrofurfuryl, isobornyl (meth)acrylate and 2-acetoacetoxyethyl methacrylate, followed by releasing the phosphonic acid groups by reaction with water or methanol, and at least one radically polymerizable, acid group-containing monomer.

2. Dental material according to claim 1 in which the radically polymerizable oligomer or polymer has a number-average molecular weight of 1,000 to 100,000 g/mol.

3. Dental material according to claim 1 in which the radically polymerizable oligomer or polymer has at least one polymerizable group which is selected from (meth)acryl, (meth)acrylamide, vinyl and allyl groups.

4. Dental material according to one of claim 3 in which the proportion of polymerizable groups in the polymer in relation to the strongly acidic groups is 60 mol.-%.

5. Dental material according to claim 1 which comprises at least one further radically polymerizable monomer.

6. Dental material according to claim 5 wherein the at least one further radically polymerizable monomer comprises a mono- or polyfunctional (meth)acrylate, a mixture of mono- or polyfunctional (meth)acrylates, or a mixture of mono- and difunctional (meth)acrylates.

7. Dental material according to claim 1 which additionally comprises an initiator for the radical polymerization.

8. Dental material according to claim 7 wherein the initiator comprises a photoinitiator or a photoinitiator in combination with a peroxide or hydroperoxide.

9. Dental material according to claim 1 which additionally comprises at least one organic or inorganic particulate filler or a mixture thereof.

10. Dental material which comprises
a) 0.1 to 30 wt-% of at least one radically polymerizable oligomer or polymer with strongly acidic phosphonic acid groups, which has a number-average molecular weight of 1,000 to 200,000 g/mol and which is prepared by
radical polymerization of at least one polymerizable phosphonate derivative which is selected from 3-(dimethoxy-phosphoryl)propyl(meth)acrylate, 3-[di(trimethylsilyl)-phosphoryl]propyl(meth)acrylate, 2-(dimethoxy-phosphoryl)ethyl (meth)acrylate, 2-[di(trimethylsilyl)-phosphoryl]ethyl (meth)acrylate, 2-[4-(di methoxyphosphoryl)-2-oxa-butyl]acrylic acid methyl ester and 2-[4-(di methoxyphosphoryl)-2-oxa-butyl]acrylic acid ethyl ester, followed by releasing the phosphonic acid groups by reaction with water or methanol, or
by radical polymerization of a monomer mixture comprising at least one of said polymerizable phosphonate derivatives and at least one comonomer which is selected from methyl, ethyl, 2-hydroxyethyl, 2-hydroxypropyl, n-butyl, benzyl, tetrahydrofurfuryl, isobornyl (meth)acrylate and 2-acetoacetoxyethyl methacrylate, followed by releasing the phosphonic acid groups by reaction with water or methanol,
b) 0.01 to 10 wt.-% initiator(s),
c) 1 to 40 wt.-% acidic radically polymerizable monomer(s),
d) 1 to 80 wt.-% radically polymerizable monomer(s), and
e) 0 to 70 wt.-% filler(s) and optionally
f) 0 to 70 wt.-% solvent.

11. Dental material according to claim 10 which comprises
a) 1 to 30 wt.-% of at least one acidic polymer,
b) 0.1 to 3.0 wt.-% initiator(s),
c) 2 to 30 wt.-% acidic radically polymerizable monomer(s),
d) 1 to 60 wt.-% radically polymerizable monomer(s), and
e) 0 to 20 wt.-% filler(s) (adhesive) or 10 to 70 wt. % filler(s) (adhesive cement) and optionally
f) 0 to 60 wt.-% solvent.

12. Dental material according to claim 10 which comprises
a) 2 to 20 wt.-% of at least one acidic polymer,
b) 0.5 to 3.0 wt.-% initiator(s),
c) 5 to 20 wt.-% acidic radically polymerizable monomer(s),
d) 5 to 50 wt.-% radically polymerizable monomer(s), and
e) 0 to 20 wt.-% filler(s) (adhesive) or 10 to 70 wt. % filler(s) (adhesive cement) and optionally
f) 0 to 50 wt.-% solvent.

13. Dental material according to claim 10 for use as adhesive or adhesive coating material which comprises
a) 0.1 to 30 wt.-% at least one acidic polymer,
b) 0.01 to 10 wt.-% initiator(s),
c) 1 to 30 wt.-% acidic radically polymerizable monomer(s),
d) 1 to 80 wt.-% radically polymerizable monomer(s),
e) 0 to 20 wt.-% filler(s), and
f) 0 to 70 wt.-% solvent.

14. Dental material according to claim 10 for use as adhesive or adhesive coating material which comprises
a) 1 to 30 wt.-% at least one acidic polymer,
b) 0.1 to 3.0 wt.-% initiator(s),
c) 2 to 30 wt.-% acidic radically polymerizable monomer(s),
d) 1 to 60 wt.-% radically polymerizable monomer(s),
e) 0 to 20 wt.-% filler(s), and
f) 5 to 60 wt.-% solvent.

15. Dental material according to claim 10 for use as adhesive or adhesive coating material which comprises
a) 2 to 20 wt.-% at least one acidic polymer,
b) 0.5 to 3.0 wt.-% initiator(s),
c) 5 to 20 wt.-% acidic radically polymerizable monomer(s),
d) 5 to 50 wt.-% radically polymerizable monomer(s),
e) 0 to 20 wt.-% filler(s), and
f) 10 to 50 wt.-% solvent.

16. Dental material according to claim 10 for use as adhesive composite cement or filling composite which comprises
a) 0.1 to 30 wt.-% of at least one acidic polymer,
b) 0.01 to 10 wt.-% initiator(s),
c) 1 to 30 wt.-% acidic radically polymerizable monomer(s),
d) 0 to 60 wt.-% radically polymerizable monomer(s), and
e) 10 to 70 wt.-% filler(s).

17. Dental material according to claim 10 for use as adhesive composite cement or filling composite which comprises a) 1 to 30 wt.-% of at least one acidic polymer,
b) 0.1 to 3.0 wt.-% initiator(s),
c) 2 to 20 wt.-% acidic radically polymerizable monomer(s),
d) 0 to 50 wt.-% radically polymerizable monomer(s), and
e) 20 to 70 wt.-% filler(s).

18. Dental material according to claim 10 for use as adhesive composite cement or filling composite which comprises
a) 2 to 20 wt.-% of at least one acidic polymer,
b) 0.5 to 3.0 wt.-% initiator(s),
c) 2 to 15 wt.-% acidic radically polymerizable monomer(s),
e) 40 to 70 wt.-% filler(s).

19. Dental material according to claim 10 for intraoral use to restore damaged teeth, for intraoral therapeutic use as dental adhesive, coating material, filling composite or cement.

* * * * *